United States Patent [19]

von Zeppelin

[11] 4,054,136
[45] Oct. 18, 1977

[54] CANNULA FOR THE INTRODUCTION OF A CATHETER

[76] Inventor: Dieter von Zeppelin, Goethestrasse 30, 7230 Schramberg 1, Germany

[21] Appl. No.: 663,204

[22] Filed: Mar. 2, 1976

[30] Foreign Application Priority Data

Mar. 3, 1975 Germany .............................. 2509139

[51] Int. Cl.² ............................................. A61M 5/00
[52] U.S. Cl. .................................. 128/214.4; 128/221; 128/DIG. 16
[58] Field of Search ............ 128/214.4, 221, DIG. 16, 128/348

[56] References Cited

U.S. PATENT DOCUMENTS

| | | | |
|---|---|---|---|
| 2,829,644 | 4/1958 | Anderson | 128/221 |
| 3,297,030 | 1/1967 | Czorny et al. | 128/214.4 |
| 3,359,978 | 12/1967 | Smith | 128/214.4 |
| 3,459,183 | 8/1969 | Ring et al. | 128/214.4 |
| 3,656,479 | 4/1972 | Huggins | 128/214.4 |
| 3,713,442 | 1/1973 | Walter | 128/214.4 |
| 3,774,605 | 11/1973 | Jewett | 128/214.4 |

*Primary Examiner*—Dalton L. Truluck
*Attorney, Agent, or Firm*—Burns, Doane, Swecker & Mathis

[57] ABSTRACT

A cannula comprises a body having a longitudinal aperture for receiving a catheter. A sealing strip formed of flexible plastic is removably disposed within the longitudinal axis to seal around the catheter. A container is removably connected to the body so as to be in fluid communication with the aperture.

6 Claims, 9 Drawing Figures

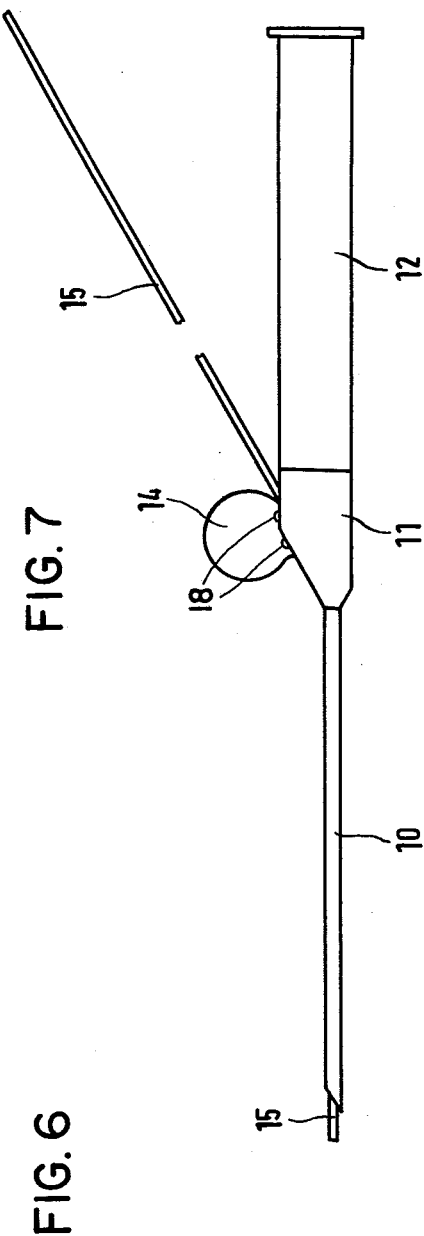

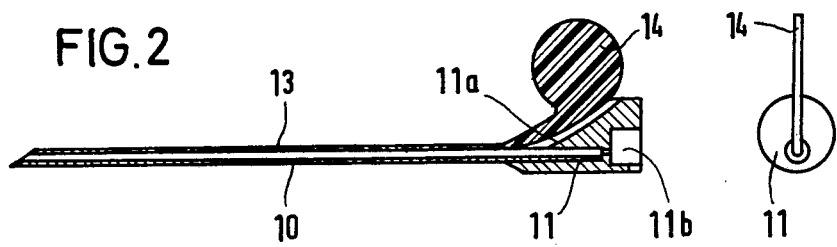
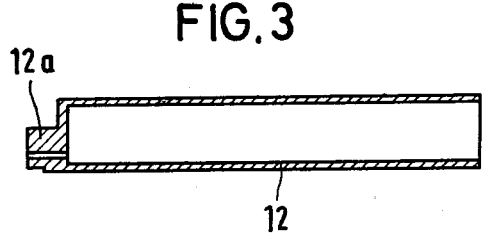 
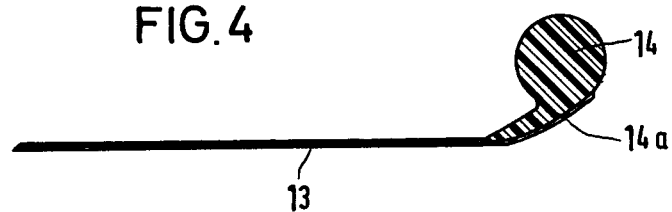
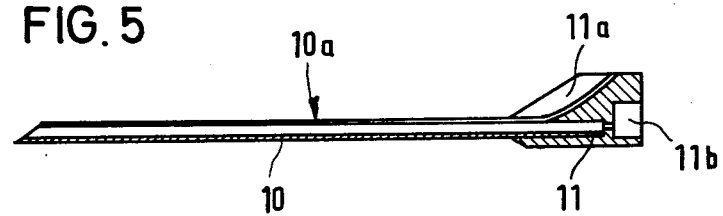

CANNULA FOR THE INTRODUCTION OF A CATHETER

The invention relates to a cannula for the introduction of a catheter, consisting of detachably interconnected, axially extending parts.

It is the object of the invention to create a cannula of the aforesaid kind that is particularly simple to manipulate. The invention accomplishes this in that the cannula is provided with a longitudinal aperture which is sealed through a sealing element of flexible plastics. The elastic sealing element may be a sealing fiber or a sealing strip closing the longitudinal aperture, onto which element may be molded a handle.

Advantageously the cannula is provided at its rear end with a grip that may have a recess for guiding the catheter. The recess in the grip can sealingly abut with the handle against the circumference of the catheter.

The invention is explained hereunder in detail with the aid of the drawing on exemplified embodiments. In the drawing are shown:

FIG. 1 is a side view of a cannula of the invention with grip and mounted container with enclosed catheter tube;

FIG. 2 is a longitudinal cut and of the cannula of FIG. 1, but without container;

FIG. 2a is a front view of the cannula of FIG. 2;

FIG. 3 is a longitudinal cut through the cannula and a front view of the container;

FIG. 3a is a front view of the container;

FIG. 4 is a side view of the sealing element only,

FIG. 5 is a side view of the cannula with grip in a longitudinal cut;

FIG. 6 is a cross-sectional view through the cannula depicting one preferred shape of the longitudinal aperture; and FIG. 7 is a cross-sectional view through the cannula depicting another preferred shape of the longitudinal aperture.

In the drawing 10 denotes the actual cannula that is equipped at its rear end with a grip 11. This grip 11 may be provided with a recess 11b into which can be inserted a projection 12a of a container 12. This container 12 is then in communication with the rear end of the cannula 10. The container may serve to hold a liquid or to hold blood.

The cannula 10 is provided with a longitudinal aperture 10a that essentially passes therethrough and that is closed by means of a sealing element, which in the illustrated instance is a sealing fiber or strip 13.

In the grip 11 is advantageously provided a recess 11a through which a catheter tube 15 may be introduced into the cavity of cannula 10. This recess 11a, that is open toward the outside, is fundamentally developed as a roughly semicircular cross-section, whereby the curvature is adaptable to the outside circumference of the catheter. This recess is closed to the outside through a handle 14, which is connected with the sealing strip 13. Also that part of handle 14 that engages in the recess 11a is provided with a groove of roughly semicircular cross-section, that is likewise adapted to the outside circumference of catheter 15. Recess 11a in grip 11 and the recess in the handle 14 thus sealingly abut against the circumference of the catheter so that any blood that may perhaps be in the cannula cannot emerge here. With the aid of this handle 14 the sealing strip 13 can be pulled in a very simple manner from the longitudinal aperture of cannula 10.

The handle 14 can be inserted with the part 14a either into the recess 11a, whereby either only a force-locking connection or also a form-locking connection exists that can only be released after overcoming a certain resistance, or the handle may also be rigidly connected with the grip, in which case then rated breaking points 18 may be provided between handle and grip which permit a separation of handle 14 from grip 11. Above all, it is important that the handle does not become involuntarily detached.

The sealing strip 13 consists preferably of an elastic plastic that is securely held in the longitudinal aperture through an appropriate design of the cannula walls which limit the longitudinal aperture 10a. These walls are advantageously provided with longitudinal flutes, e.g. in the form of an U at 16 in FIG. 6, or a V at 17 in FIG. 7, which cause a form-locking connection between the cannula 10 and correspondingly configured the sealing strips 13a, 13b respectively.

Naturally the longitudinal aperture 10a must be so dimensioned in its width that the catheter tube 15 can be sideways taken out from the cannula. But expediently the longitudinal aperture 10a is less wide than the diameter of the cannula so that the catheter tube 15 is securely held in the cannula and has to be somewhat deformed during its lateral removal.

The use of a distinctly elastic material for the sealing fiber is, however, not imperative. The material may also be plastically workable or may also be essentially hard, always provided that it is possible to remove the sealing strip without difficulty from the longitudinal aperture.

I claim:

1. A cannula for the introduction of a catheter, comprising:
    an elongated body having a pointed forward end and slot means extending substantially the full length of said body, and an enlarged grip disposed at the rearward end of said body;
    said grip including a recess therein extending laterally from said slot means and communicating with said slot means and adapted to guide the catheter into said slot means;
    a plastic strip removably disposed in said body;
    said strip including a first portion in said slot means and extending throughout said slot means for closing said slot means, and a handle portion secured within said recess to laterally close said recess, so that said handle and grip sealingly surround a catheter inserted within the cannula;
    said handle portion including means to be gripped for removing said strip from said body;
    said grip further including a bore which fluidly communicates with, and forms an extension of said slot means; and
    a container removably connected to said grip in communication with said bore for receiving fluid from said slot means.

2. A cannula according to claim 1 wherein said slot means includes walls having longitudinal flutes which mate with said strip to resist removal of said strip from said aperture.

3. A cannula according to claim 2 wherein said flutes are U-shaped.

4. A cannula according to claim 2 wherein said flutes are V-shaped.

5. A cannula according to claim 1 wherein said handle portion is releasably inserted within said grip.

6. A cannula according to claim 1 wherein said handle portion and said grip are provided with a frangible connection whereby said strip can be removed from said recess and slot means.

* * * * *